United States Patent [19]
Newman

[11] Patent Number: 5,082,979
[45] Date of Patent: Jan. 21, 1992

[54] CYMENOL PREPARATION BY DIRECT DEHYDROGENATION

[75] Inventor: Christopher P. Newman, Canterbury, Great Britain

[73] Assignee: Unilever Patent Holdings B.V., Rotterdam, Netherlands

[21] Appl. No.: 578,496

[22] Filed: Sep. 6, 1990

[30] Foreign Application Priority Data

Sep. 6, 1989 [GB] United Kingdom ............... 8920110
Nov. 30, 1989 [GB] United Kingdom ............... 8927072

[51] Int. Cl.$^5$ ............................................. C07C 37/06
[52] U.S. Cl. ................................... 568/782; 568/781
[58] Field of Search ............ 512/25, 20; 568/814, 568/830, 782, 781

[56] References Cited

U.S. PATENT DOCUMENTS

| | | | |
|---|---|---|---|
| 2,361,532 | 10/1944 | Cox | 568/814 |
| 2,366,409 | 1/1945 | Johnston | 568/814 |

FOREIGN PATENT DOCUMENTS

47478 1/1918 Finland ............................ 568/814

OTHER PUBLICATIONS

Arctander, "Perfume and Flavor Chemicals", vol. 1 (1969), #573.
Arctander, "Perfume and Flavor Chemicals", vol. 11 (1969), #2944.

*Primary Examiner*—Werren B. Lone
*Attorney, Agent, or Firm*—Cushman, Darby & Cushman

[57] ABSTRACT

The invention relates to a process for the conversion of 8-hydroxymenthenes into 8-hydroxycymenes by treating the 8-hydroxymenthenes in the vapor phase with a dehydrogenation catalyst, e.g. palladium. The process is preferably carried out at 80°–150° C. The hydroxymenthene vapor is preferably passed through the catalyst system at a pressure below 8 kPa and/or with the aid of an inert gas or vapor. Oxygen may be present as a hydrogen acceptor. The process is particularly suitable for converting 8-hydroxy-p-menth-1-ene into 8-hydroxy-p-cymene. The reaction products are of value as intermediates in the preparation of fragrance chemicals.

15 Claims, 1 Drawing Sheet

CYMENOL PREPARATION BY DIRECT DEHYDROGENATION

FIELD OF THE INVENTION

The present invention relates to the production of intermediates suitable for the preparation of fragrances. In particular, this invention relates to improvements in the production of 8-hydroxycymenes which are of value as intermediates in the preparation of fragrance chemicals.

BACKGROUND OF THE INVENTION

Important substances in the preparation of perfumes are fragrances of the indane and tetralin musk type such as 7-acetyl-1,1,3,4,4,6-hexamethyltetralin. These substances have excellent odour and fixative properties. They are stable to alkali and light, soluble in most solvents, substantially colourless and persistent and are also relatively cheap. They are commonly prepared by acetylation of the corresponding methyl-substituted indane or tetralin in a Friedel-Crafts reaction. In turn, many routes have been proposed for the preparation of these latter substances. Several have been proposed involving the formation of an alicyclic attachment to substituted cymenes which in turn may be obtained from 8-hydroxycymene.

It is known from U.S. Pat. No. 2,366,409 (Hercules) that 8-hydroxymenthene can be converted in the liquid phase to a mixture of 8-hydroxycymene and 8-hydroxymenthane by means of a disproportionation reaction. This reaction appears to be a combination of hydrogenation and dehydrogenation i.e. is a transfer hydrogenation. For every molecule of 8-hydroxymenthene which is dehydrogenated, enough hydrogen is produced to hydrogenate two molecules of 8-hydroxymenthene to 8-hydroxymenthane.

The Hercules reaction results in an approximate 2:1 mixture of respectively 8-hydroxymenthane and 8-hydroxycymene. We have confirmed the teaching in the Hercules patent that the pressure at which the reaction is carried out makes little difference to this ratio and pressures as low as 0.4 kPa at 73° C. (reflux temperature) in the liquid phase will still give an approximate 2:1 ratio of products.

BRIEF SUMMARY OF THE INVENTION

In contrast, we have now found that by carrying out the above reaction in the vapour phase, the ratio of the resulting, above mentioned products is altered, giving a higher yield of 8-hydroxycymene, and a correspondingly lower yield of 8-hydroxymenthane. The proportion of 8-hydroxycymene produced by the dehydrogenation can be increased by selecting optimum conditions for the dehydrogenation reaction.

Accordingly, the invention provides a process for the conversion of 8-hydroxymenthenes to 8-hydroxycymenes which comprises treating an 8-hydroxymenthene in the vapour phase with a dehydrogenation catalyst.

DETAILED DESCRIPTION OF THE INVENTION

Figure 1:
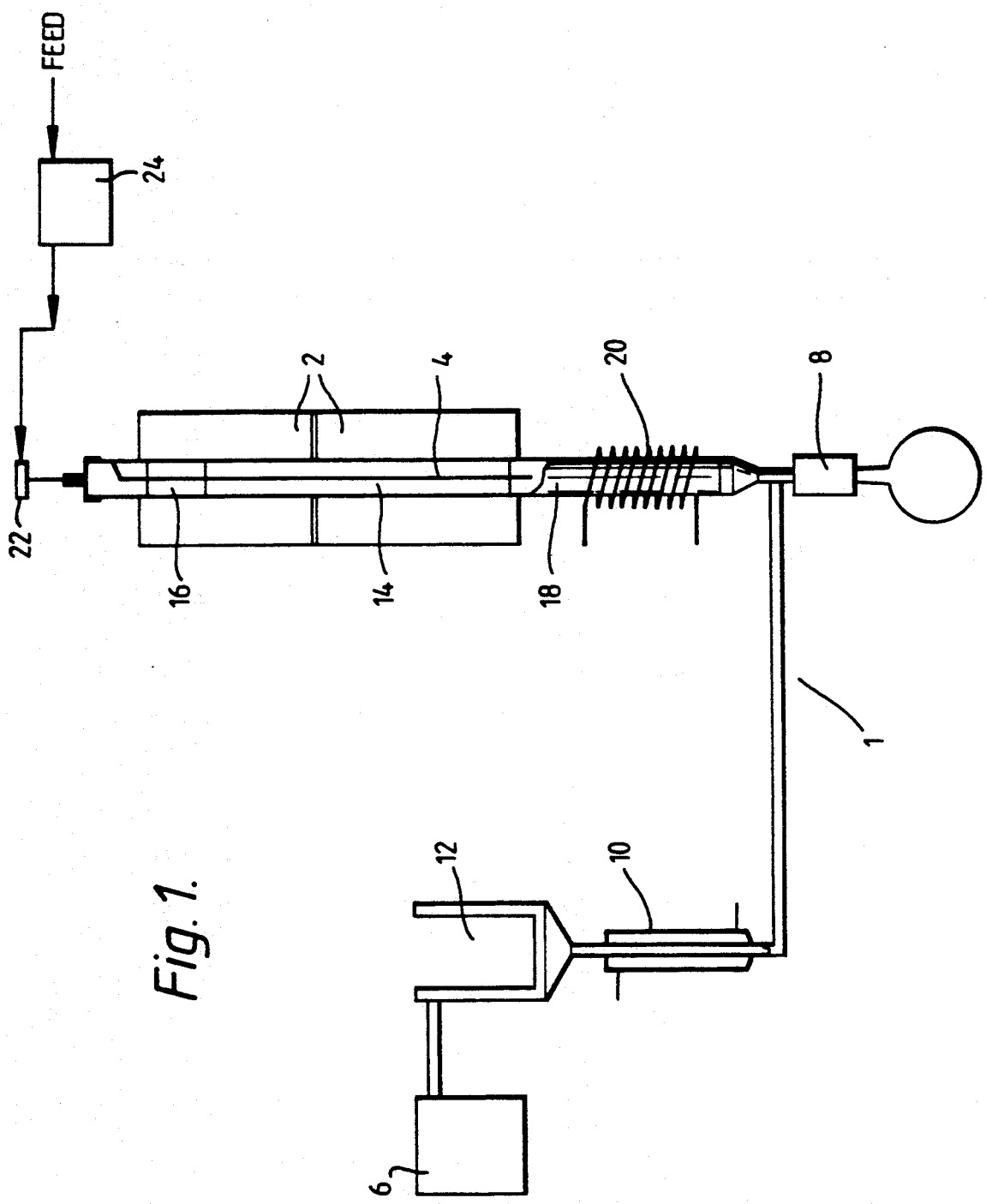

The starting material for the method in accordance with this invention may be any 8-hydroxymenthene. The carbon structure of the menthenes will be found in Bernthsen, Textbook of Organic Chemistry, Sudborough Revision, 1922 edition D. Van Nostrand Company, New York, N.Y., page 609 and page 613. The system of numbering the carbon atoms shown there will be utilized herein. It will be appreciated that the methyl group represented by carbon No. 7 may be para, ortho or meta with respect to the isopropyl group. 8-Hydroxymenthadienes are included within the term 8-hydroxymenthene.

The hydroxymenthene may be in the form of a pure compound, or it may be in the form of a mixture, e.g. a distillation cut reasonably rich therein. For example, 8-hydroxy-p-menth-1-ene (alpha-terpineol) may be utilized in a fairly pure state, or it may be utilized in the form of ordinary commercial pine oil, which is usually a mixture of terpene alcohols. It will be understood that where the 8-hydroxymenthenes utilized have the para-menthene configuration, as is the case with 8-hydroxy-p-menth-1-ene, the derivatives will have the same para arrangement. Similarly, ortho- and meta-hydroxy-menthenes lead to ortho and meta products respectively.

It is a feature of the invention that the conversion takes place in the vapour phase, in contrast to previous conversions which were carried out in the liquid phase. Surprisingly, we have found that by carrying out the conversion in the vapour phase, yields of the desired 8-hydroxycymene are increased, and the catalyst lifetime may be extended.

Different methods are available to achieve the vapour phase, for example the temperature of the 8-hydroxymenthene feedstock can be raised above its boiling point, which for alpha-terpineol is about 220° C. at atmospheric pressure. However, carrying out the conversion at a temperature of above 150° C. may result in dehydration and formation of undesirable by-products. The desired vapour phase may be achieved at a lower temperature by reducing the pressure preferably to below 8 kPa, more preferably from 0.1 to 5 kPa, and most preferably from 0.1 to 0.65 kPa. Alternatively, the vapour phase may be achieved by vaporizing the substrate with the aid of an inert carrier gas e.g. nitrogen, or vapour e.g. steam or mixtures thereof. The use of controlled, low pressure or a carrier gas or vapour also serves to remove hydrogen gas produced during the conversion from the reaction system, thereby minimising the production of 8-hydroxymenthane.

The conversion is preferably carried out at a temperature of from 80° to 150° C., more preferably between 130° and 145° C., and for 8-hydroxy-p-menth-1-ene most preferably takes place at about 142° C. The reaction system can be maintained at the desired temperature using any heat transfer system for example hot oil or steam.

It is also desirable that acid is excluded from the reaction system, to prevent dehydration of the alcoholic material.

The catalyst is preferably a metal of Group VIII in activated form, particularly palladium but e.g. platinum, ruthenium, rhodium, iridium or osmium may be used. They may be supported on e.g. silicas, alumina or carbon, suitably at levels of from 0.1 to 10% by weight. A particularly suitable catalyst is 0.2% by weight palladium on an alumina support, available commercially e.g. as Engelhard PGCS2. A base additive, for example an amine, may be added to maintain an acid free system. The catalyst is preferably pre-washed with a base solution.

Air or oxygen may be introduced into the system; oxygen acts as a hydrogen acceptor, removing the free hydrogen from the system as water vapour. Other suitable hydrogen acceptors may be used.

Formation of water is highly exothermic and care is needed in the control of the reaction temperature. Therefore, when air or oxygen is introduced into the system it is desirable to operate the conversion at a pressure of less than 5 kPa at which pressure combinations of oxygen and hydrogen present a less hazardous mixture. Alternatively, mixtures of air or oxygen with an inert gas or vapour as mentioned above may be used. Thus, not only is the substrate vaporized but also the transfer of hydrogen to the hydrogen acceptor is controlled.

The invention is further illustrated by the following Examples.

EXAMPLE 1

Distillation through a packed bed

This method uses a modified bench distillation apparatus wherein the substance is distilled through a catalyst bed. The latter comprises 30 g of Engelhard PGCS2 catalyst (0.2% by weight Palladium on alumina spheres (eggshell)).

The distillation flask is charged with 8-hydroxy-p-menth-1-ene (86% by weight pure, 126.9 g equivalent to 0.7 mol), sodium carbonate (6.3 g) and triethylamine (3.2 g). The latter is to neutralise any acid sites on the reaction catalyst. Sodium carbonate is included to minimise acid catalysed dehydration of the substrate in the flask. The reactor section is heated electrically to a temperature of 140° C. and the pressure in the apparatus lowered to 0.64 kPa. The material is distilled slowly through the reactor at an average rate of 0.91 g/min maintaining the catalyst bed temperature in the range 132°-141° C. and the pressure at 0.64 kPa.

A total of 114.7 g of material was collected and this was analysed by quantitative gas-liquid chromatography and shown to contain the following:

P-cymene: 3.9% by wt (4.47 g, 33 mmol)
8-hydroxy-p-menth-1-ene: 18.3% by wt (21.0 g, 136 mmol)
8-hydroxy-p-cymene: 45.2% by wt (51.8 g, 346 mmol)
8-hydroxy-p-menthane: 32.6% by wt (37.4 g, 239 mmol)

There remained 10.2 g of residue, 4.4 g of material was collected in a cold trap (−78° C.) and 6.4 grams of material were not condensed in the system.

Conversion of 8-hydroxy-p-menth-1-ene: 80.6%
Selectivity for 8-hydroxy-p-cymene: 61%
Yield based on theory: 49%

EXAMPLE 2

Tubular Reactor

This method uses a tubular stainless steel reactor (1) (see schematic diagram, FIG. 1), capable of operating under reduced pressure and equipped with heaters (2), central thermocouple well (4), and connected to a vacuum pump (6) via a fraction cutter (8), condenser (10) and cold trap (12). The stainless steel reactor, internal diameter 25 mm, is packed with 156 g of Engelhard PGCS2 catalyst (0.2% by weight Palladium on alumina spheres (eggshell)). On top of the catalyst bed (14) is a section (16) packed with glass helices to act as a flash heater. The catalyst bed length is 45 cm and the flash heater length is 10 cm. Beneath the catalyst bed is a section (18) packed with knitmesh with an exterior cooling coil (20) to act as a condenser. Prior to use the reactor containing the catalyst is filled with 0.2% by weight sodium hydroxide solution and left to stand for a minimum of 2 hours. It is then washed with distilled water until neutral to pH paper. This treatment removes any acid sites from the reactor/catalyst that would give rise to significant amounts of p-cymene by dehydration/dehydrogenation. The temperature has to be carefully controlled and kept below 150° C. for the same reason. The column is operated at an exhaust pressure of approximately 0.5 kPa and 8-hydroxy-p-menth-1-ene is introduced into the reactor using a feed pump (24) via a pressure sustaining valve (22) set at 170 kPa (to prevent feed being sucked in).

The reaction conditions are as follows:
exit pressure 0.4–0.6 kPa
temperature 132°-140° C.
feed rate 1.4–1.7 ml/min When the reactor conditions have stabilised, the substrate is delivered to the top of the column. Condensed product from the reactor is collected via the fraction cutter (8). After the appropriate running period, the feed pump (24) is switched off and the column allowed to drain. The heaters (2) are switched off and the reactor allowed to cool to below 40° C. The system is then raised to atmospheric pressure under nitrogen.

Out of a total of 11708 g of 8-hydroxy-p-menth-1-ene (93% pure) fed into the reactor, 11651 g of product were collected. The yield of products, expressed as % relative peak area (rpa) from gas chromatographic analysis, was as follows:

|  | % rpa |
| --- | --- |
| 8-hydroxy-p-cymene | 50–60 |
| 8-hydroxy-p-menth-1-ene | 2.6–8 |
| 8-hydroxy-p-menthane | 30–40 |
| p-cymene | 0.5–7.0 |

EXAMPLE 3

The method of Example 1 was repeated at several different temperatures, while maintaining the outlet pressure at 0.65 kPa. The results were as follows:

| Temp (°C.) | p-cymene % | 8-hydroxy-P-menth-1-ene % | 8-hydroxy-p-menthane % | 8-hydroxy p-cymene % |
| --- | --- | --- | --- | --- |
| 93 | 0.7 | 32.4 | 38.4 | 27.4 |
| 103 | 0.4 | 40.0 | 32.7 | 26.0 |
| 115 | 0.8 | 30.9 | 24.0 | 33.3 |
| 117 | 1.8 | 19.3 | 36.5 | 41.5 |
| 127 | 1.5 | 27.3 | 32.3 | 38.1 |
| 139 | 4.0 | 17.8 | 33.9 | 44.7 |
| 149 | 17.7 | 22.9 | 24.8 | 26.0 |

It can be seen that, at low pressure, increasing the temperature gave increased levels of 8-hydroxy-p-cymene. However, at some point around 139° C. the increase in temperature leads to an increasing amount of p-cymene due to dehydration/dehydrogenation of the substrate alcohol.

EXAMPLE 4

The method of Example 2 was repeated at several different pressures, while maintaining the temperature at 140° C. The results were as follows:

| Pressure kPa | p-cymene % | 8-hydroxy-p-menth-1-ene % | 8-hydroxy-p-menthane % | 8-hydroxy p-cymene % |
|---|---|---|---|---|
| 0.4 | 6.0 | 2.6 | 36.9 | 54.1 |
| 1.3 | 7.7 | 2.1 | 41.9 | 45.6 |
| 2.6 | 7.3 | 3.0 | 42.5 | 43.4 |
| 6.5 | 8.4 | 1.9 | 43.7 | 44.4 |

It can be seen that the ratio of 8-hydroxy-p-cymene to 8-hydroxy-p-menthane is greater than 1:1 when the reaction is carried out at lower pressures.

EXAMPLE 5

This method uses a fixed bed reactor similar to that shown for Example 2 (FIG. 1), but modified as follows: the column is of glass construction of internal diameter 25 mm and is fitted with an outer jacket enabling the reactor to be heated with hot oil. The reactor is packed with 120 g of Engelhard PGCS2 catalyst (0.2% Palladium on alumina spheres (eggshell)) giving a catalyst bed length of 35 cm. Fitted to the top of the reactor is a wiped film evaporator into which the 8-hydroxymenthene and inert gas or vapour can be fed. This evaporator is modified such that vapour mixture generated in it can be fed directly into the reactor. The reactor exhaust is fitted with a suitable condensing system and collecting vessel. Prior to use the reactor containing the catalyst is filled with 0.2% sodium hydroxide solution and left to stand for a minimum of 2 hrs. It is then washed with distilled water until neutral to pH paper. This treatment removes any acid sites from the reactor/catalyst that would give rise to significant amounts of p-cymene through dehydration/dehydrogenation. To avoid the same side reaction, the temperature has to be carefully controlled and kept below 150° C. In this method steam at 100° C. of the desired supply rate is fed directly to the top of the evaporator. The feedstock is also fed to the top of the evaporator using a metering pump set to the desired feed rate. The evaporator jacket is set at 140° C. and the reactor jacket at 140° C.

8-Hydroxy-p-menth-1-ene (302 g) is fed into the system at atmospheric pressure under the following conditions:

temperature reactor centre 132°–135° C.
    feed rate (8-hydroxy-p-menth-1-ene) 1.83 g/min
    feed rate (steam) 16.4 g/min The product condensed from the exhaust gas stream consists of an organic layer (260.7 g) and an aqueous layer containing some dissolved products (2740 g). The composition of the separated layer and the water soluble material after extraction with chloroform (2×200 ml) is given below (% gc relative peak area).

| Products | Separated | Extracted | Total proc. |
|---|---|---|---|
| Mass | 260.7 g | 33.4 g | 294.1 g |
| 8-hydroxy-p-cymene | 59.8% | 68.6% | 60.8% |
| 8-hydroxy-p-menth-1-ene | 4.1% | 3.3% | 4.0% |
| 8-hydroxy-p-menthane | 32.4% | 24.8% | 31.6% |
| cymene | 1.9% | 1.1% | 1.8% |

The total mass of organic material recovered is 294.1 g, that is 97.3% of the organic material fed to the evaporator.

I claim:

1. A process for the conversion of an 8-hydroxymenthene to an 8-hydroxycymene which comprises treating the 8-hydroxymenthene in the vapour phase with a dehydrogenation catalyst, wherein the conversion is carried out at a temperature of from 80° to 150° C.

2. A process according to claim 1 wherein the 8-hydroxymenthene is 8-hydroxy-p-menth-1-ene.

3. A process as claimed in claim 1 wherein the dehydrogenation catalyst comprises a Group VIII metal.

4. A process as claimed in claim 3 wherein the dehydrogenation catalyst comprises palladium.

5. A process as claimed in claim 1 wherein the conversion is carried out at a temperature of from 130° to 145° C.

6. A process as claimed in claim 1 wherein the conversion is carried out at a pressure of less than 8 kPa.

7. A process as claimed in claim 6 wherein the conversion is carried out at a pressure of from 0.1 to 5.0 kPa.

8. A process as claimed in claim 7 wherein the conversion is carried out at a pressure of from 0.1 to 0.65 kPa.

9. A process as claimed in claim 1 wherein the 8-hydroxymenthene is introduced into the catalyst system by means of an inert gas or vapour.

10. A process as claimed in claim 9 wherein the inert vapour is steam.

11. A process as claimed in claim 1 wherein the conversion is carried out in the absence of acid.

12. A process as claimed in claim 11 wherein the conversion is carried out in the presence of added base.

13. A process as claimed in claim 1 wherein air or oxygen is added with the 8-hydroxymenthene to act as a hydrogen acceptor.

14. A process for the conversion of 8-hydroxy-p-menth-1-ene to 8-hydroxy-p-cymene wherein 8-hydroxy-p-menth-1-ene is treated in the vapour phase with a dehydrogenation catalyst comprising palladium, at 130°–145° C. in the absence of acid and the presence of oxygen, at a pressure of below 8 kPa.

15. A process for the conversion of 8-hydroxy-p-menth-1-ene to 8-hydroxy-p-cymene wherein 8-hydroxy-p-menth-1-ene is treated in the vapour phase with a dehydrogenation catalyst comprising palladium, at 130°–145° C. in the absence of acid and the presence of oxygen wherein the 8-hydroxy-p-menth-1-ene is introduced in the catalyst system by means of steam.

* * * * *